US007313976B2

(12) United States Patent
Swain et al.

(10) Patent No.: US 7,313,976 B2
(45) Date of Patent: Jan. 1, 2008

(54) TECHNIQUES FOR DYNAMICALLY TESTING AND EVALUATING MATERIALS AND COATINGS IN MOVING SOLUTIONS

(76) Inventors: Geoffrey Swain, 473 Young St., Melbourne, FL (US) 32935; Arthur Touzot, 1227 Palm Place Dr., Palm Bay, FL (US) 32905

( * ) Notice: Subject to any disclaimer, the term of this patent is extended or adjusted under 35 U.S.C. 154(b) by 23 days.

(21) Appl. No.: 10/973,028

(22) Filed: Oct. 25, 2004

(65) Prior Publication Data

US 2006/0016250 A1  Jan. 26, 2006

Related U.S. Application Data

(60) Provisional application No. 60/517,341, filed on Nov. 5, 2003.

(51) Int. Cl.
*G01N 17/00* (2006.01)
(52) U.S. Cl. .............................. 73/865.6; 73/86; 73/866
(58) Field of Classification Search .................... 73/86, 73/54.28, 866, 865.6; 366/142, 282, 283
See application file for complete search history.

(56) References Cited

U.S. PATENT DOCUMENTS 4,859,073 A * 8/1989 Howseman et al. ........ 366/195
4,884,892 A * 12/1989 Gust ........................... 366/136
5,049,492 A * 9/1991 Sauer et al. ................... 435/30
2003/0034305 A1* 2/2003 Luehmann et al. ......... 210/646
2005/0087002 A1* 4/2005 Kanzaki et al. ............ 73/54.28

FOREIGN PATENT DOCUMENTS

JP          09021676 A  *  1/1997

* cited by examiner

*Primary Examiner*—Hezron Williams
*Assistant Examiner*—Paul M West
(74) *Attorney, Agent, or Firm*—Allen, Dyer, Doppelt, Milbrath & Gilchrist, P.A.

(57) ABSTRACT

The dynamic testing of materials in moving solutions, such as anti-fouling paint in seawater, is conducted in a cylindrical tank. A stirrer having a drive shaft and one or more paddles or blades is driven by a variable speed motor to rotate and to impart rotational velocity to a liquid, which passes over the test materials which are attached to the periphery of the tank. The flow conditions over the surface can be well characterized. The surface of the test materials may be instrumented to measure physical, chemical and hydrodynamic conditions. The energy required for testing is reduced over prior art techniques.

1 Claim, 4 Drawing Sheets

TECHNIQUES FOR DYNAMICALLY TESTING AND EVALUATING MATERIALS AND COATINGS IN MOVING SOLUTIONS

CROSS REFERENCE TO RELATED APPLICATIONS

This application is related to U.S. provisional application 60/517,341, filed Nov. 5, 2003, by Geoffrey Swain and Arthur Touzot, the contents of which are hereby incorporated by reference in their entirety. In addition, this application claims priority to that provisional application.

STATEMENT REGARDING FEDERALLY SPONSORED RESEARCH OR DEVELOPMENT

The invention described herein was submitted as an expansion to office of Naval Research Contact N00014-02-1-0216, pursuant to its long range scientific and technology program BAA 03-001.

BACKGROUND OF THE INVENTION

1. Field of the Invention

The invention is directed to techniques for testing and evaluating materials and coatings and, more particularly, to testing and evaluating materials and coatings in moving solutions.

2. Description of Related Art

The techniques of the invention as well as the techniques the prior art are intended to measure the performance of materials exposed to flowing solutions, such as seawater, at velocities designed to subject the material to shear stresses experienced in service. For example the measurement of the performance of antifouling paints under dynamic conditions is necessary to help in assessment of anti-fouling paint film thicknesses required for fouling control between dry dockings of ships, in the selection of materials, in quality assurance, and in understanding performance mechanisms.

Test data derived from such measurements can be used to serve as a guide for predicting the service life of anti-fouling paints in order to calculate the necessary paint thickness to fit specified deployment cycles. The aging of anti-fouling paints in service will vary depending on such factors as: berthing location, geographic area of operation, salinity, pH, and temperature of seawater. One should also note that some areas of a ship are subject to differing hydrodynamic conditions.

Several methods have been developed in the prior art for the dynamic aging of antifouling paints. These include high flow flumes, rotating drums, rotating discs and rotating cylinders. None, however, offer an economic, efficient and well-calibrated system that enables hydrodynamic, physical and chemical conditions to be measured at the material surface. A summary of prior art methods, their characteristics, advantages and disadvantages are presented below.

ASTM D4938 Erosion Testing Of AF Paints Using High Velocity Water (high speed water channel):

The high velocity water tunnel consists of a large pump which forces water through a four-sided rectangular section with diminishing width to generate water flows of up to 18 m/s. For example, the Naval Research Lab Key West facility uses a 950 gpm pump and a 5.5 in high rectangular cross section with widths of 3.28, 1.64, 1.09, 0.82, 0.66, and 0.55 in which generate water velocities of 5, 10, 15, 20, 25, and 30 knots respectively. The advantage of this system is that it is an already established ASTM method and it has been shown to effectively challenge coating systems at a high water velocities. The disadvantages, however, are many. The design requires a large horsepower pump to achieve the high velocity of water flows due to inefficiencies caused by large pressure losses in the system. The system is expensive to build. The system is not suited to test a large number of samples as it can only accommodate one test panel at each velocity. The flow characteristics are poorly defined. The narrow width (0.55 in) required to generate high water velocities preclude the testing of panels with large macrofouling communities.

ASTM D4939 Subjecting Marine AF Coating To Biofouling And Fluid Shear Forces In Natural Seawater (rotating drum):

The rotating drum is the most commonly employed method used to imitate the dynamic flow conditions experienced on a ship hull and they have provided much useful information to the industry. The method requires that a drum with diameter greater than 18 in be rotated in natural seawater at velocities calculated to generate the desired hydrodynamic shear stress. Large diameter drums are capable of testing several panels at a time, however, the panels are usually small and require a curvature to match the radius of the drum which make then unsuitable for subsequent hydrodynamic testing in water, tunnels or boats. The systems require large horsepower motors and are energy inefficient due to losses to the surrounding water. The flow characteristics are also usually poorly defined.

Rotating Disk:

The rotating disk is an established laboratory method that has been used to generate some useful data. The flow characteristics, however, are complex and variable across the test surface and this makes it difficult to use the data to model for full-scale prediction performance.

BRIEF SUMMARY OF THE INVENTION

The invention is directed towards techniques that dynamically test and evaluate materials and coating in moving solutions, which overcome the problems of the prior art discussed above.

A circular tank is utilized to contain a liquid to be utilized during the testing. An example of such a liquid might be seawater. Substantially rigid rectangular panels are inserted into the tank and positioned so that top and bottom connect to points on the inner circumference of the tank. Thus, test panels are not required to have a circular shape conforming to the diameter of the tank. Rather, they maintain their planar shape. Materials to be tested are applied or attached to the test panel holder so that they are at or beneath the surface of the liquid contained in the circular tank. A motor driven stirrer has one or more paddles which emanate from a center point of rotation so that as the paddles turn, they cause the seawater to rotate and impart a rotational velocity to the liquid in the circular tank.

DETAILED DESCRIPTION OF THE INVENTION

Figure 1:
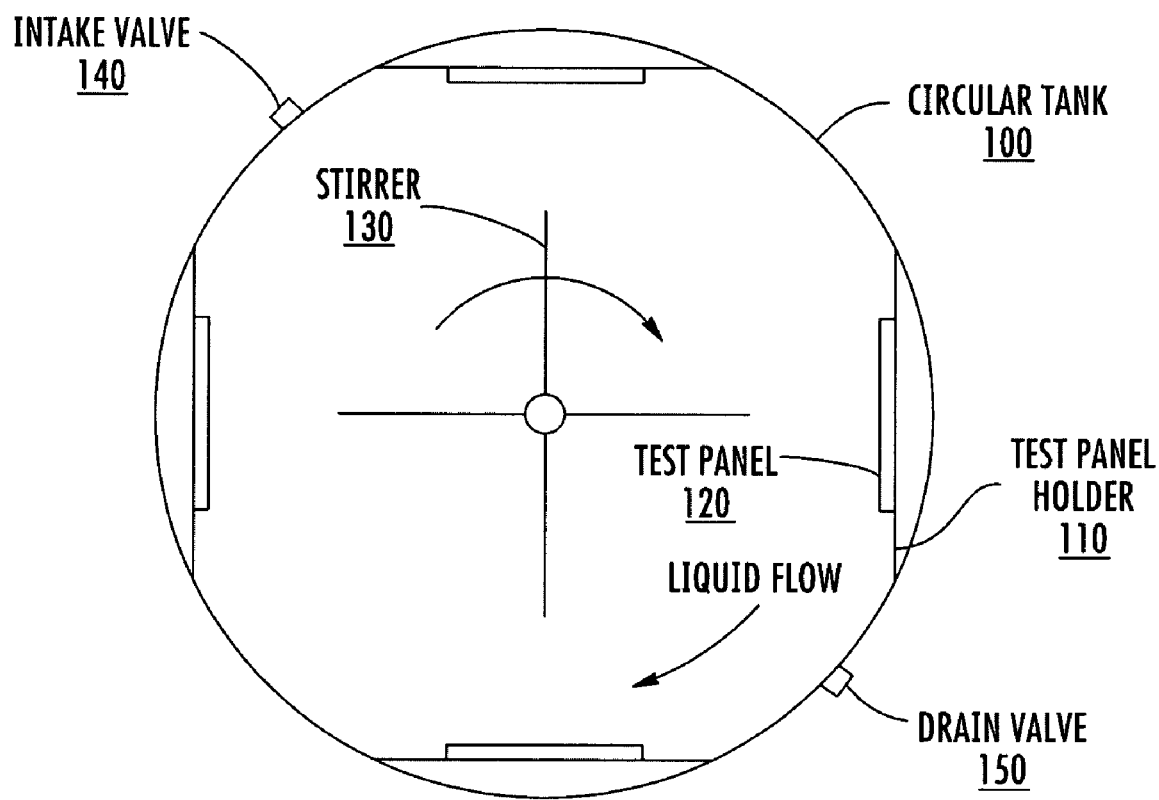
FIG. 1 is a top view of a test tank showing operational interactions in accordance with one aspect of the invention.

FIG. 1 is a top view of a test tank showing operational interactions in accordance with one aspect of the invention. In FIG. 1, a circular tank 100 is utilized to contain a test liquid, such as seawater. Seawater can be placed in the tank either from the open top or through optional intake valve 140 and may be drained from the tank either by siphoning out or through use of optional drain valve 150. In implementations where a continuous supply of fresh seawater is required, the intake valve may be opened to allow new seawater to be received and the drain valve may simultaneously open to allow an equivalent amount of seawater to drain from the tank. The water intake and outflow from the tank can be controlled automatically to maintain a given level of the fluid within the tank. One way of controlling the amount of seawater within the tank would utilize a float, connected to a switch, which would activate the drain valve 150 when water exceeded a certain level.

Attached to the walls of the circular tank are test panel holders 110. In the example shown, four different test panels are located around the inner circumference of the tank. The test panel holders 110 can be attached to the walls of the tank with bolts and a resilient seal. Of course, the selection of bolt and seal materials must resist corrosion from the liquid utilized in the test tank. Such bolt and seal combinations are known in the prior art and maybe arranged in combinations like unto those utilized to mount the water tank to a commode. The test panel holder 110 is designed to receive test panels 120 and to hold them in place during testing. The preparation of panels for testing can be that described in ASTM International article D 4938-89.

Before or after the test panels have been put in place, the tank may be filled with the test liquid. With the test panels in place, a stirrer and drive assembly are mounted over the top of the tank, as described more hereinafter.

The stirrer 130 is shown in FIG. 1. In operation, with the panels in place and the tank filled, the stirrer begins rotation in a way, which causes a circular flow of liquid within the tank. The velocity of liquid substantially matches the rotational velocity of the stirrer as it runs in the tank. By controlling the rotational velocity of the stirrer 130, one can control the velocity of the test liquid passing over the test panels 120.

On initial start-up, the stirrer begins slowly rotating and causing the liquid within the tank to rotate with it. The speed of rotation can increase more or less continuously until the desired velocity is achieved. Once the desired velocity is achieved, given the angular momentum that the seawater has achieved by virtue of being driven by the stirrer, the energy required to maintain the velocity of seawater passing across the test panels 120 is considerable reduced. It is reduced because the only energy that needs to be supplied to the test liquid is the energy needed to overcome losses that occur during rotation of the stirrer. Unlike previous test methods, which require large motors and to increase the velocity of the liquid from zero to the desired velocity on a continuous basis, the energy required in accordance with the invention is only that required to overcome losses as the liquid rotates. This results in a substantial savings and in the utilization of much lower powered motors.

It may be desirable to monitor certain parameters during testing. These can include salinity, pH, temperature, velocity of the test liquid and the like. Instrumentation for making such measurements can be mounted to the side of the tank or to the framework for mounting the stirrer and drive assembly to the tank.

Figure 2:
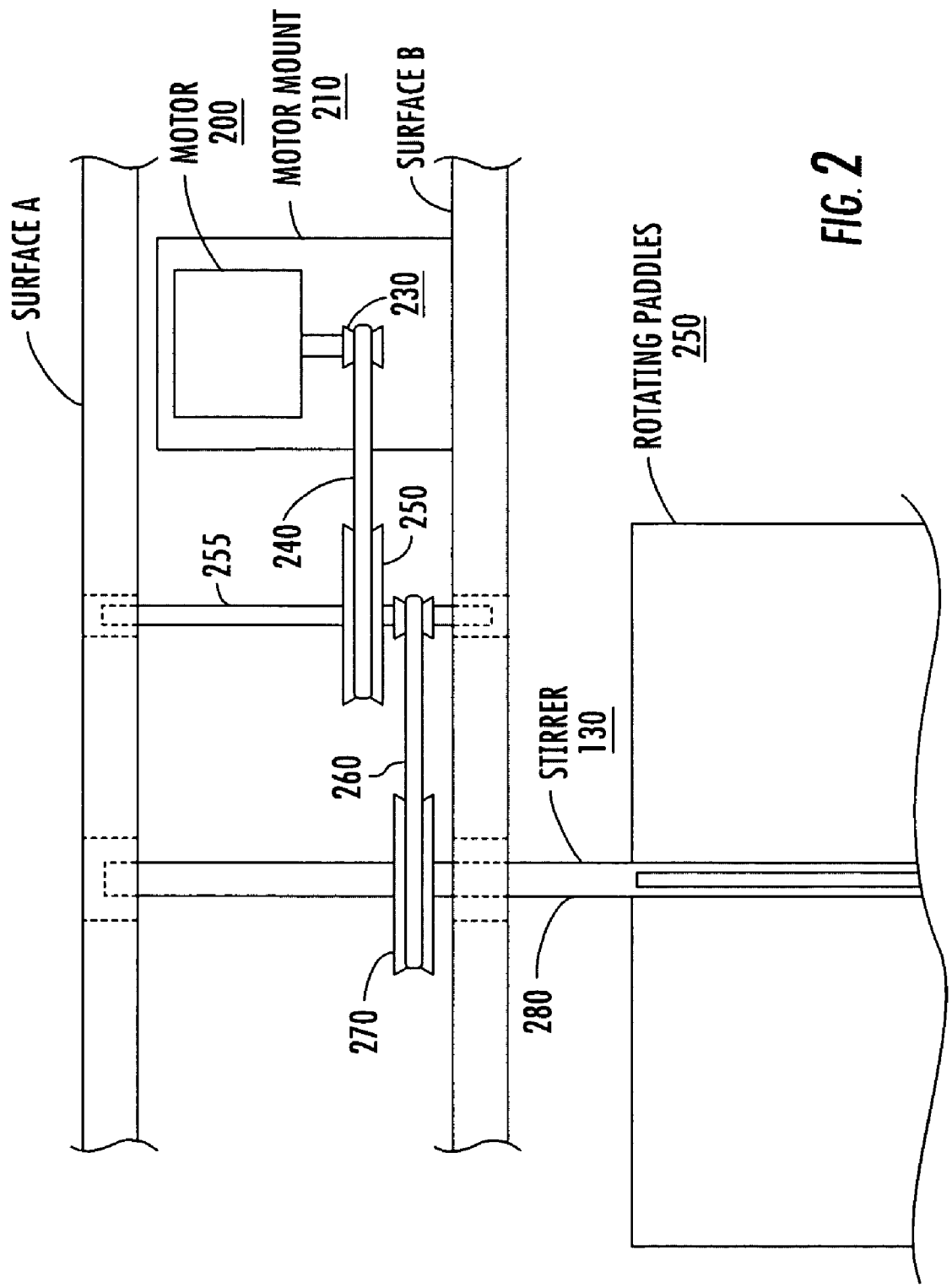
FIG. 2 shows a side view of a stirrer and drive mechanism in accordance with one aspect of the invention.

FIG. 2 shows a side view of a stirrer and drive mechanism in accordance with one aspect of the invention.

As shown in FIG. 2, a stirrer 130 has a number of paddles 290, connected to drive shaft 280 for rotation. When the drive shaft 280 turns, the paddles are forced to rotate and, when placed in a tank containing liquid, to cause the liquid in the tank to rotate with it. A drive mechanism for causing the drive shaft 280 to turn is illustrated in FIG. 2. A motor 200, such as a variable speed motor, is mounted with the drive shaft vertically positioned on a motor mount 210. A pulley 230 on the drive shaft of the motor 200 is connected by a drive belt 240 to turn a larger pulley 250, which is connected to a drive shaft 255 journaled to permit rotation between two planar pieces of mounting material, such as wood or steel. The drive shaft 255 can be mounted so that the ends can rotate freely in bearings that are mounted within the mounting materials.

The drive shaft 255 also drives a smaller pulley, which is connected by drive belt 260 to a large pulley 270 connected to drive shaft 280 of the stirrer. Note the drive shaft 280 penetrates through the lower planar mounting material and goes all the way into the upper planar mounting material where it is allowed to rotate freely in a bearing. Similarly, a bearing or other mechanism allows the drive shaft 280 to rotate freely within the lower planer mounting material.

In operation, the motor 200 turns the pulley 230 which causes the pulley 250 to rotate which causes the smaller pulley attached to drive shaft 255 to rotate which then connects to the larger pulley 270 which turns the drive shaft 280 causing the rotating paddles 290 to rotate imparting velocity to the liquid within the tank.

The rotating paddles 290 may optionally have one or more openings in the paddle to facilitate the development of turbulence. With the use of a variable speed motor, the velocity of the liquid can be controlled to allow for selection of a variety of test conditions.

Figure 3:
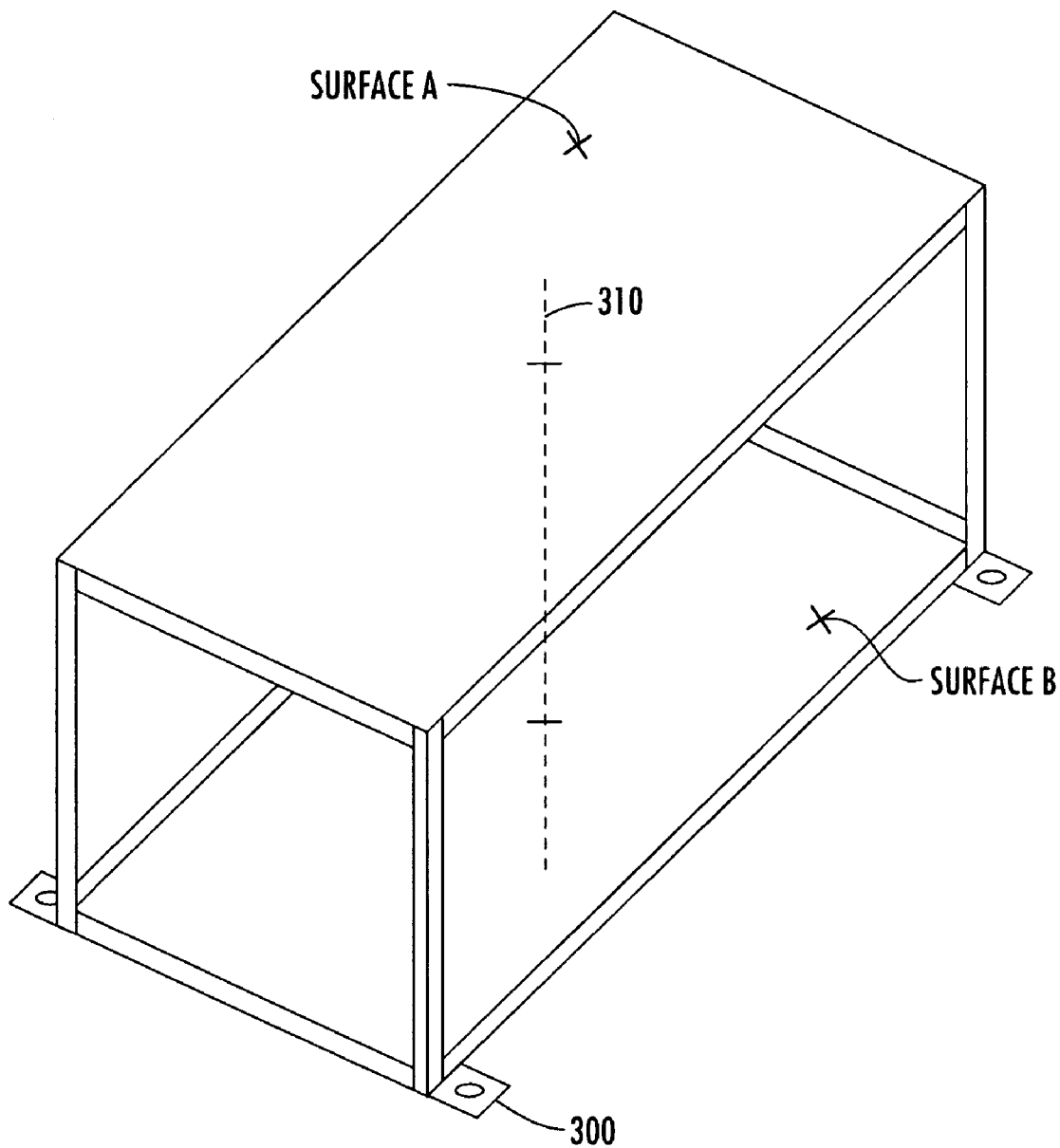
FIG. 3 shows a framework for mounting the stirrer and drive mechanism in accordance with one aspect of the invention.

FIG. 3 shows a framework for mounting the stirrer and drive mechanism in accordance with one aspect of the invention.

As shown in FIG. 2, the drive mechanism for the stirrer mounts between two planar sheets of mounting material such as wood or steel. These two sheets of planar mounting material can be contained in a framework such as that shown in FIG. 3. A centerline for the drive shaft 280 is illustrated at 310. The other components are positioned an appropriate distance away from the centerline of the drive shaft 280 in order to achieve the driving functionality described in conjunction with FIG. 2. The framework for the stirrer assembly has four tabs 300 positioned on the outside for mounting to a framework surrounding the tank itself as described more hereinafter.

Figure 4:
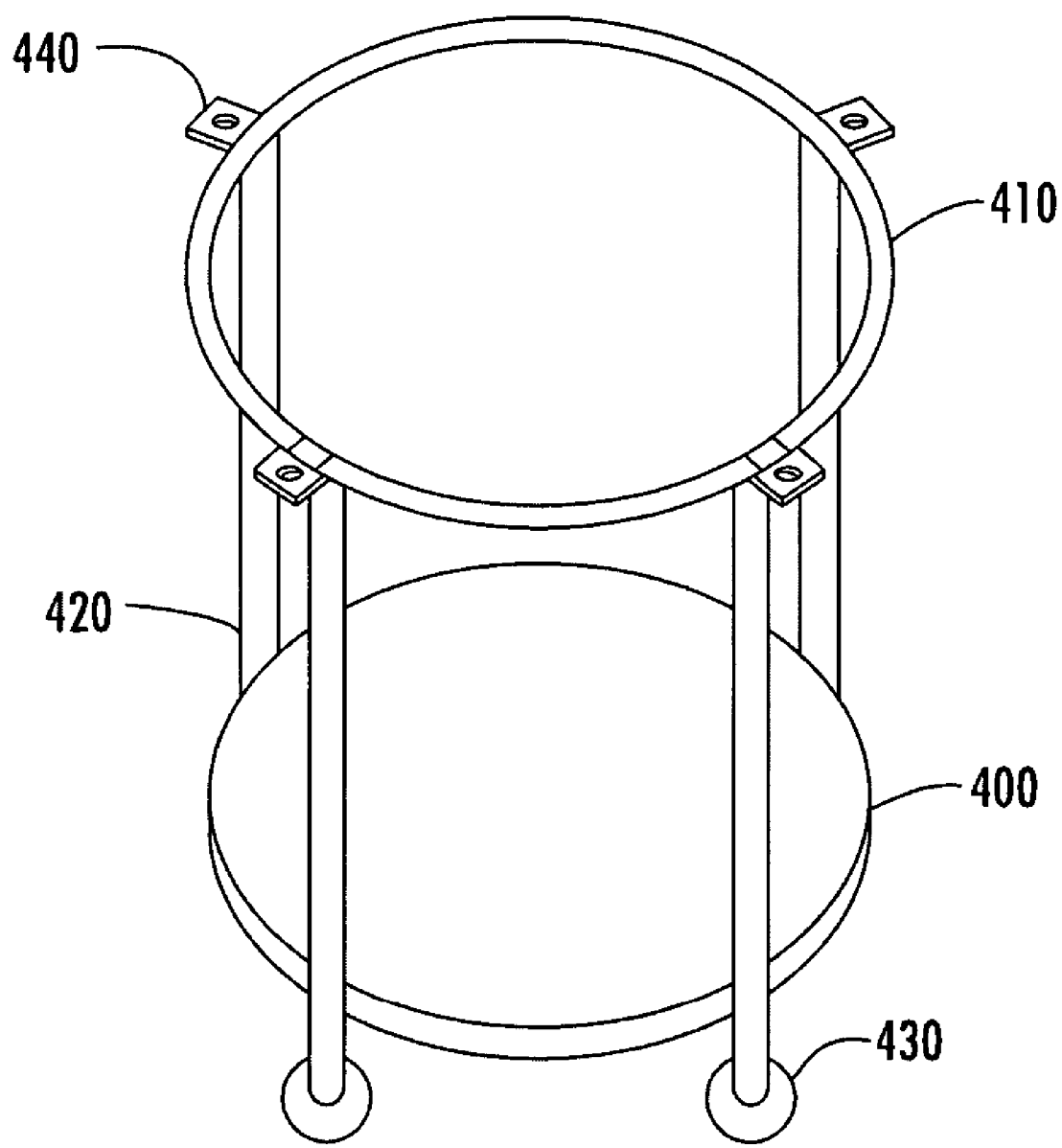
FIG. 4 shows a framework for containing the test tank in accordance with one aspect of the invention.

FIG. 4 shows a framework for containing the test tank in accordance with one aspect of the invention. In the embodiment shown, the upper portion of the tank framework contains a circular band 410 designed to encircle the tank near its top. A base 400 provides a surface on which the tank can sit. A set of casters 430 permit the tank framework to be readily moved. This is particularly convenient when the tank is in position and partially or completely filled with the test liquid. The casters are optional, and if not utilized, the base 400 need not particularly be a solid piece but rather can be another metal strap sized so as to receive the base of the tank. The tank could then sit directly on the ground. In the example shown, four vertical struts 420 connect the base 400 with the upper band 410 and provide a measure of reinforcement to the sides of the tank so that the tank does not distend and conceivably rupture during aggressive testing. A number of vertical struts is optional and can be selected depending on the usage intended.

A number of tabs 440 are shown connected to the upper tank ring 410. These tabs 440 are utilized for connecting the stirrer framework so as to be positioned solidly over the tank during the testing.

Some tanks are constructed so that there is an upper lip that might extend beyond the tabs shown with the tank situated in position within the framework. In such instances, one may wish to provide an angular piece, which would allow the mounting tabs to extend all the way to the top of the tank without interfering with the lip so that the stirrer framework can be mounted to be flush with the top of the tank. This can be done by welding an angular piece to the vertical strut and/or to the circular ring 410 so that the tabs 440 end up flush with the upper most portion of the tank.

In operation, with the test panels in place and the tank assembled and filled with test liquid, the testing can begin. Some tests require alternating static and dynamic cycles of approximately 30 days each for a total length of time or until some degree of fouling is reached. The tank may be filled with natural seawater taken at a site where a fouling rate is high. The seawater can flow through the tank during the static period allowing the test panels to become fouled. When the conditions for terminating the static interval have been satisfied, the dynamic cycle can begin by causing the stirrer to stir the seawater past the test panels in a way of which simulates actual operational conditions of a ship underway. The dynamic phase can run for a desired length of time or may be stopped periodically and test measurements made of the effectiveness of the ablative coating in causing removal of the marine fouling.

The invention described herein is not limited to the specific examples shown, but rather as a broad applicability to communications generally.

What is claimed is:

1. A method of saving energy when testing the impact of moving liquid on materials comprising the step of exposing a test material to a liquid rotationally circulating in a tank in which the step of exposing a test material comprises applying the test material to a planar panel and placing the panel in the tank so that the top and bottom of the panel substantially form a chord of a circle tracking the inside surface of the tank.

* * * * *